(12) United States Patent
Reek et al.

(10) Patent No.: US 8,283,276 B2
(45) Date of Patent: Oct. 9, 2012

(54) COORDINATION COMPLEX SYSTEM COMPRISING TAUTOMERIC LIGANDS

(75) Inventors: Joost Nikolaas Hendrik Reek, Amersfoort (NL); Frederic William Patureau, Fourqueux (FR); Mark Kuil, Leusden (NL); Albertus Jacobus Sandee, Utrecht (NL); Jurjen Meeuwissen, Amsterdam (NL)

(73) Assignee: Universiteit van Amsterdam, Amsterdam (NL)

( * ) Notice: Subject to any disclaimer, the term of this patent is extended or adjusted under 35 U.S.C. 154(b) by 159 days.

(21) Appl. No.: 12/744,293

(22) PCT Filed: Nov. 19, 2008

(86) PCT No.: PCT/EP2008/065840
§ 371 (c)(1),
(2), (4) Date: Sep. 20, 2010

(87) PCT Pub. No.: WO2009/065856
PCT Pub. Date: May 28, 2009

(65) Prior Publication Data
US 2011/0003959 A1    Jan. 6, 2011

(30) Foreign Application Priority Data
Nov. 22, 2007  (EP) .................................. 07121317

(51) Int. Cl.
B01J 31/00 (2006.01)
C07F 15/00 (2006.01)
C07C 231/12 (2006.01)
C07C 67/303 (2006.01)
C07C 45/69 (2006.01)
C07C 5/10 (2006.01)
C07D 209/08 (2006.01)
C08G 69/08 (2006.01)

(52) U.S. Cl. ............................. 502/155; 502/103; 528/9
(58) Field of Classification Search ..................... None
See application file for complete search history.

(56) References Cited

U.S. PATENT DOCUMENTS
2002/0095049 A1    7/2002   Monsees et al.

FOREIGN PATENT DOCUMENTS
EP             1 201 673 A1    5/2002
(Continued)

OTHER PUBLICATIONS
Abstract cited in SciFinder for Foss et al., Zhurnal Obshchei Khimii, 1983, vol. 53, Issue11, pp. 2489-2496, 1983.*
(Continued)

*Primary Examiner* — Melvin C Mayes
*Assistant Examiner* — Yun Qian
(74) *Attorney, Agent, or Firm* — Gilberto M. Villacorta; Sunit Talapatra; Foley & Lardner LLP

(57) ABSTRACT

The invention relates to a coordination complex system comprising a ligand having the formula: $R_1$—$SO_2$—NH—P$(XR_2)_2$ (1a); or $R_1$—$SO_2$—N=PH $(XR_2)_2$ (1b); or $R_1$—SO(OH)=N—P$(XR_2)_2$ (1c); wherein X is independently O, S, NH, or a bond; $R_1$ and $R_2$ are independently selected from hydrogen and substituted or unsubstituted alkyl or aryl; wherein at least one equivalent of the ligand is complexed to an equivalent of a metal selected from a transition metal and lanthanide. The invention also relates to the use of said coordination complexes as catalysts in the hydroformylation, hydrogenation, transfer hydrogenation, hydrocyanation, polymerization, isomerization, carbonylation, cross-coupling, metathesis, CH activation, allylic substitution, aldol condensation, or Michael addition.

10 Claims, 2 Drawing Sheets

FOREIGN PATENT DOCUMENTS

WO WO-2004/103559 12/2004

OTHER PUBLICATIONS

Hetterscheid et al., "Rhodium-Mediated Stereoselective Polymerization of Carbenes," Journal of American Chemical Society, vol. 128, No. 30, 2006, pp. 9746-9752.

Jiang et al., "An ONIOM study of amines adsorption in H-[Ga]MOR," Journal of Molecular Catalysis A: Chemical, vol. 232, 2005, pp. 59-67.

Lefort et al., "Instant Ligand Libraries. Parallel Synthesis of Monodentate Phosphoramidites and in Situ Screening in Asymmetric Hydrogenation," American Chemical Society, Organic Letters, vol. 6, No. 11, 2004, pp. 1733-1735.

Van Den Berg et al., "Rhodium/MonoPhos-Catalysed Asymmetric Hydrogenation of Enamides," Advan. Synth. Catal., vol. 344, No. 9, 2002, pp. 1003-1007.

International Search Report received in corresponding International Application No. PCT/EP2008/065840.

* cited by examiner

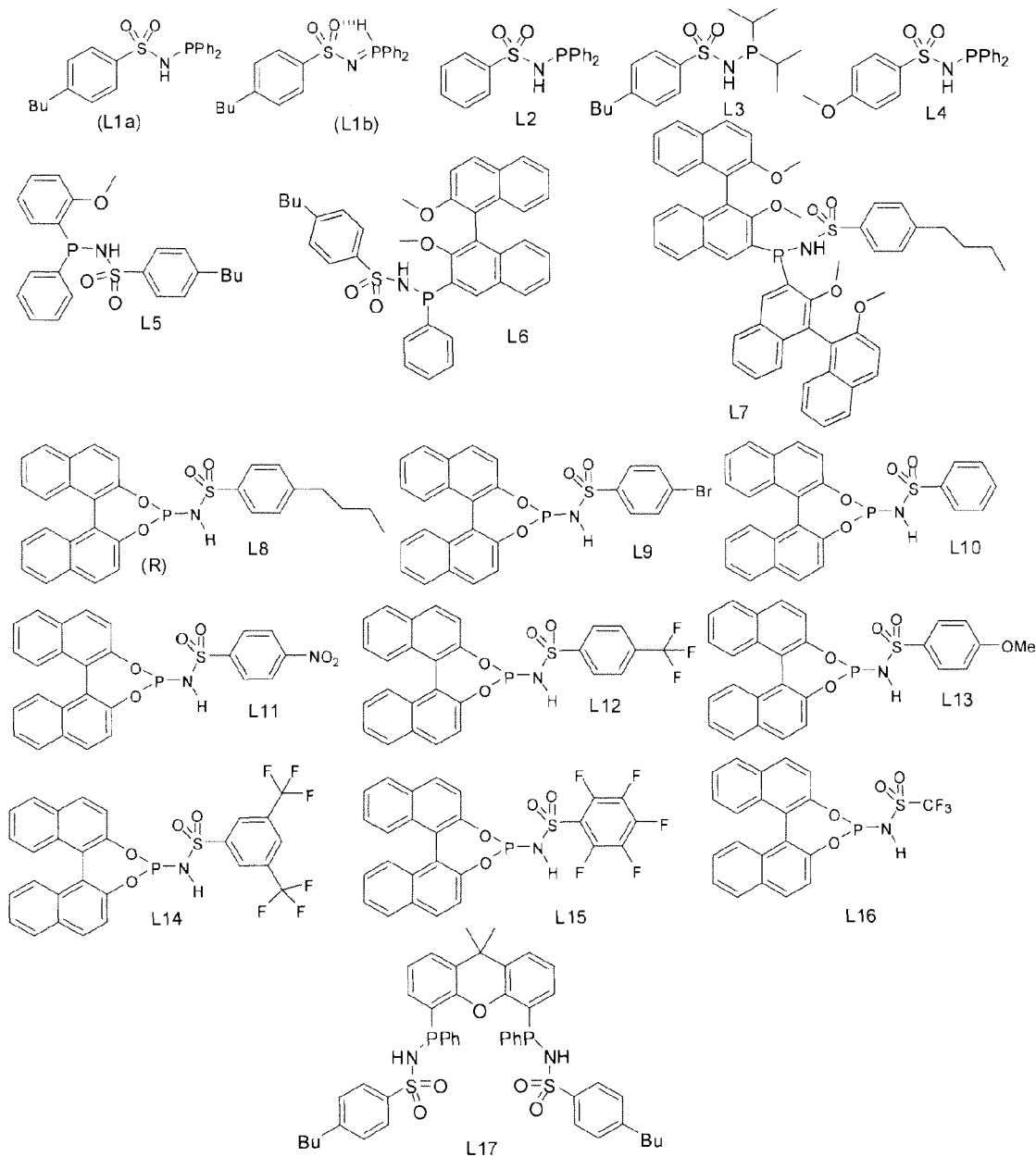
Figure1 (examples of ligands having formula 1)

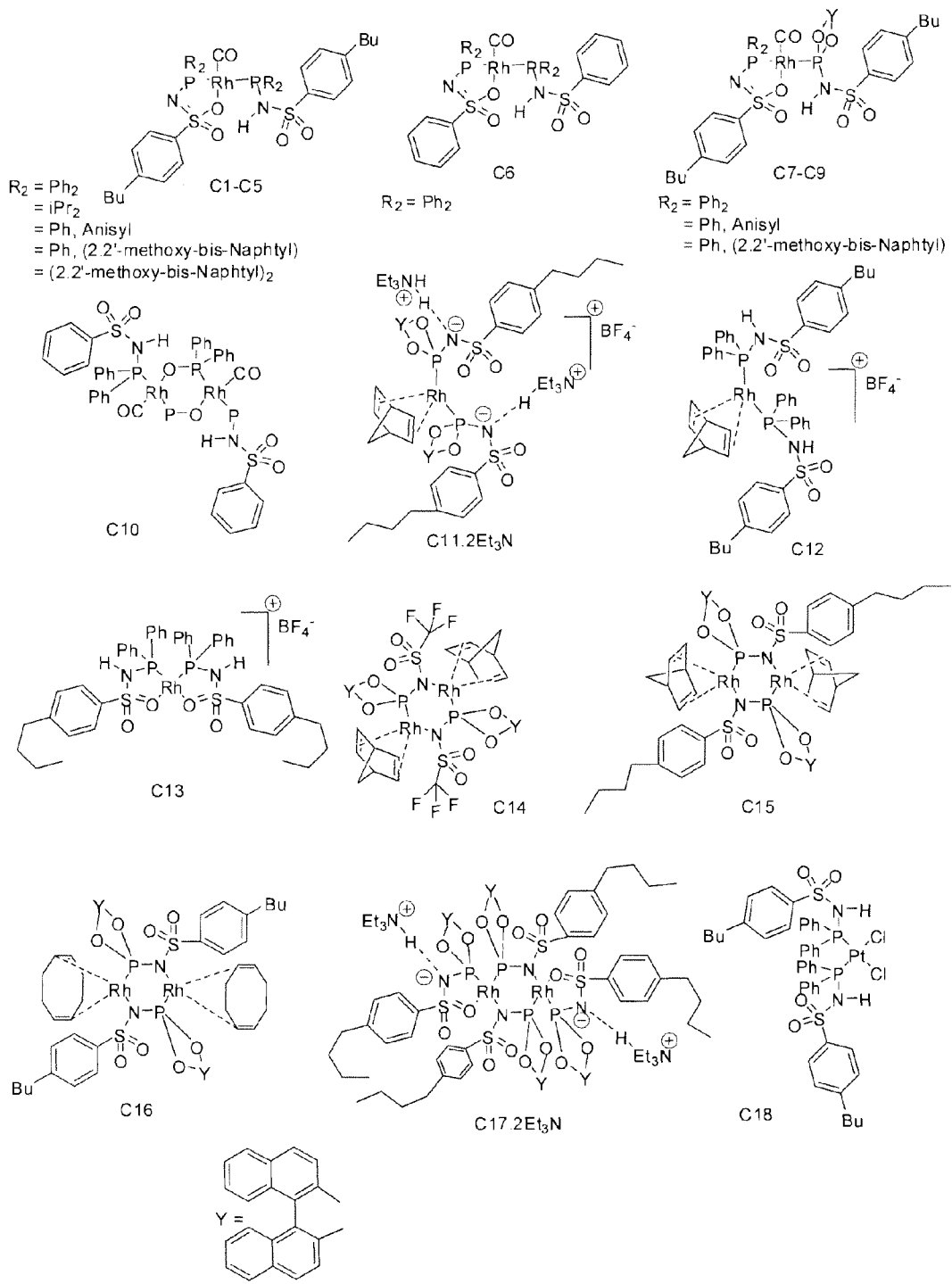
Figure 2 of specific examples containing a ligand of type 1:

COORDINATION COMPLEX SYSTEM COMPRISING TAUTOMERIC LIGANDS

This is a National Stage application of PCT/EP2008/065840, filed Nov. 19, 2008, which claims priority to European Application No. 07121317.7, filed Nov. 22, 2007. The foregoing application is incorporated by reference herein in its entirety.

The invention relates to a coordination complex system comprising a ligand which is complexed to at least a metal selected from a transition metal or lanthanide, to a catalyst system comprising said coordination complex system, and to the use of said coordination complex system as a catalyst.

Bidentate ligands represent an important class of ligands for transition metal catalysis, however, their synthesis is often tedious and time consuming compared to their monodentate counterparts. Combinatorial approaches to catalyst discovery are therefore mostly based on monodentate ligands. In WO 2004/103559 supramolecular ligands have been identified as a new class of ligands that form by a self-assembly process of ligand building blocks through specific interactions. These ligands have bidentate character, are modular in nature and are synthetically accessible, and therefore highly promising when applied in combinatorial approaches for rapid catalyst discovery. Here we disclose, a new generation of hydrogen bonded supramolecular multidentate ligands based on sulfonamide derivatives that are adaptive to the environment of transition metals, by means of tautomerization. The invention pertains to a coordination complex system comprising a ligand having the formula: $R_1$—$SO_2$—NH—$P(XR_2)_2$ (1a); or $R_1$—$SO_2$—N=PH$(XR_2)_2$ (1b); or $R_1$—SO(OH)=N—P$(XR_2)_2$ (1c); wherein X is independently O, S, NH, or a bond; wherein $R_1$ and $R_2$ are independently selected from substituted or unsubstituted alkyl and aryl; wherein at least one equivalent of the ligand is complexed to an equivalent of a metal selected from a transition metal and lanthanide.

BRIEF DESCRIPTION OF THE DRAWINGS

FIG. 1 shows examples of ligands according to formula 1.

FIG. 2 shows examples of coordination complex systems comprising ligands according to the invention.

The term "ligand" will further mean the compound that may have formula (1a), (1b), (1c), or a mixture thereof. L1, L2, L3, L4, etcetera mean examples of the ligand. $R_1$ and $R_2$ are preferably independently selected from hydrogen, alkyl, aryl, substituted alkyl and substituted aryl. Substituents include alkyl, aryl, nitro, trialkylsilyl, and halogens for aryl groups and halogen for alkyl groups. Two moieties $R_2$ together can form a divalent aryl, or a substituted divalent aryl. Preferably the complex comprises two equivalents of ligand, wherein X is preferably a bond or oxygen.

Preferably alkyl is $C_{1-6}$ alkyl. The alkyl substituent is halogen, most preferably fluoro, such as to obtain $R_1$ is $CF_3$. Preferred aryl for $R_1$ is phenyl. Preferred aryl substituents are nitro, $C_{1-6}$ alkyl, $CF_3$, halogen, tri-$C_{1-4}$ alkylsilyl, and $C_{1-6}$ alkoxy. $R_2$ preferably is aryl, more preferably phenyl, naphthyl, bisphenyl, or bisnaphthyl. These aryl groups may be substituted by one or more of nitro, $C_{1-6}$ alkyl, $CF_3$, halogen, tri-$C_{1-4}$ alkylsilyl, and $C_{1-6}$ alkoxy. Most preferably these aryl groups are unsubstituted or substituted with a methoxy group.

If two moieties $R_2$ together form a divalent aryl or a substituted divalent aryl, then preferably X=O. Preferred embodiments of the aryl moiety of divalent aryl groups are phenylene, naphthylene, bisphenylene, and bisnaphthylene. These divalent aryl groups can be substituted by $C_{1-6}$ alkyl, tri-$C_{1-4}$ alkylsilyl, $CF_3$, halogen, and $C_{1-6}$ alkoxy groups. The most preferred $C_{1-6}$ alkoxy group is methoxy. Two ligands, if each of these ligands contains at least one $R_2$ which is an aryl group, may also be connected to each other through said two aryl groups, preferably phenyl groups, wherein said aryl groups are connected to each other by one or two linking moieties, such as O, N, S, or one or two carbon atoms. The N is bonded to H or $C_{1-6}$ alkyl, and the carbon atom or atoms are bonded to H and/or $C_{1-6}$ alkyl. Examples of such carbon linking moieties are methylene, 2,2-propylidene, and 1,2-ethylene.

The ligands of the invention can be prepared by a simple condensation reaction of a sulfonamide, for instance para-n-butylphenylsulfonamide to a phosphine halide, such as $Ph_2PCl$. In solution these sulfonamide phosphorous compounds may exist in different tautomeric forms, i.e. ligands (1a), (1b), and (1c). These tautomeric forms can in some cases be detected as the different tautomers being in slow exchange on the NMR time scale. The tautomerization is crucial for its coordination behavior and gives rise to the formation of hydrogen bonded homo- and hetero-bidentate ligands, and the corresponding metal complexes are for instance found to be very efficient in the asymmetric catalytic processes.

The three tautomers of the ligand (1a, 1b, 1c) and formation of complex (3) with Rh(acac)(CO)$_2$ is shown in Scheme 1.

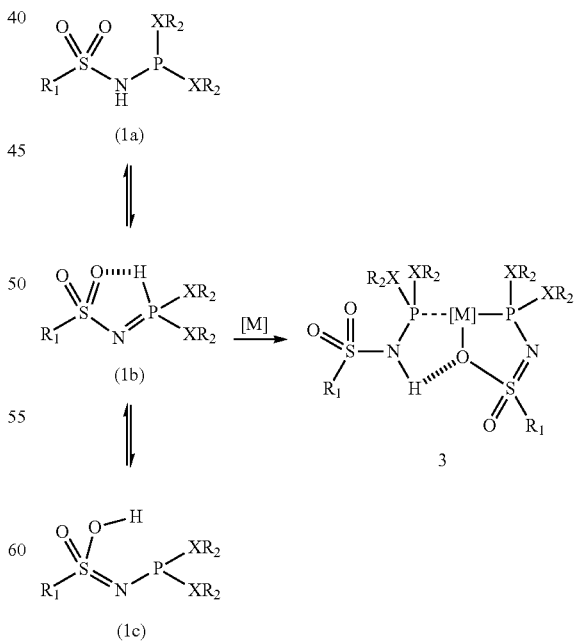

Scheme 1

An example of these tautomers and their complex formation is given in Scheme 2

Scheme 2

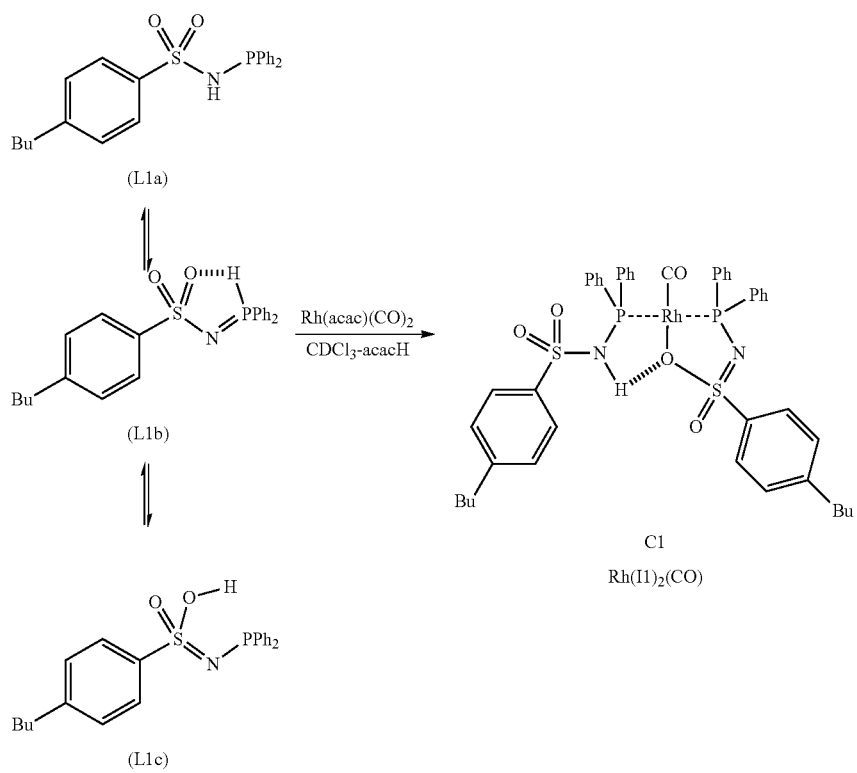

In the example of Scheme 2, the addition of two equivalents of the ligand (L1) to a CDCl$_3$ solution of Rh(acac)(CO)$_2$ gives complex C1 having two different tautomers of the ligand coordinated in trans position about the metal center as is shown in the typical AB pattern in $^{31}$P NMR with large P—P coupling. The deprotonated form of ligand (L1c) likely coordinates to the metal in a P—O chelate fashion, which is also observed by dft-calculations. The ligand tautomers (L1a) and (L1c) at the metal center can be identified through their coupling pattern in NMR.

The hydrogen bond interaction between ligands(L1a) and (L1c) coordinated to the metal was confirmed by IR spectroscopy showing the concentration independent NH vibration at 3281 cm$^{-1}$ which is typically shifted compared to the free NH (3341 cm$^{-1}$). Using rhodium as metal the NH NMR shift of Rh(L1a,L1c)(CO) is concentration independent, whereas the free ligand (L1a) shows concentration dependent NMR shift of the NH proton. This indicates that the free tautomer (L1a) self-associates at higher concentrations. Further obtained examples of this type include (FIG. 2): C2 through C6 (complex 2 to complex 6).

Hetero-ligated metal complexes can be made by complexing two different ligands to the metal. An example of this is depicted in Scheme 3. A solution of (L1), (L8) and Rh(acac)(CO)$_2$ in a 1:1:1 ratio yields pure Rh(L8.L1)(CO)(complex C7) having the ligands in a trans geometry (AB system in the $^{31}$P NMR). Further examples of this type obtained include (FIG. 2): C8 through C10.

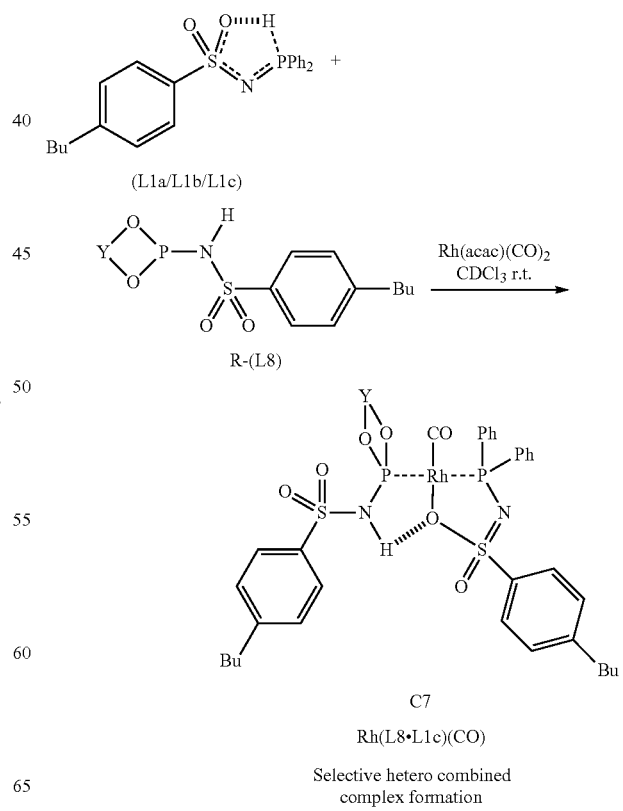

Scheme 3

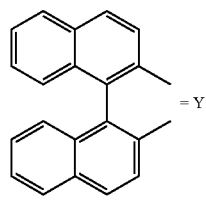

Further, cationic complexes can be obtained of the type 4 (Scheme 4) by complexing two equivalents of the ligand to one equivalent of a cationic metal precursor. Still further, in defined cases, type 5 complexes can be obtained upon exposing type 4 complexes to an atmosphere of $H_2$ (Scheme 4).

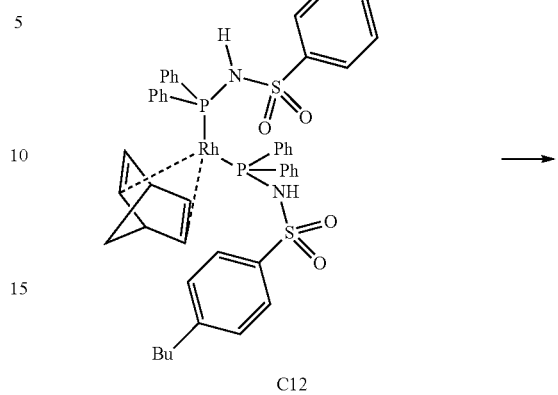

C12

Scheme 4

[Scheme 4 diagram showing structures 1, 4, 5, 6, 7]

An example of a type 4 and type 5 complex is depicted in Scheme 5, i.e. C12 and C13 respectively. In this example two equivalents of L1 were added to one equivalent of [Rh(COD)$_2$](BF$_4$) to yield C12. Upon exposing this complex to a $H_2$-atmosphere C13 was obtained quantitatively. Further examples of type 4 complexes obtained include rhodium complex C12 and platinum complex C18 (Chart FIG. 2).

Scheme 5

[Scheme 5 showing L1a reacting with [Rh(NBD)$_2$](BF$_4$) to form C13]

C13

In other defined cases the exposure of type 4 complexes to $H_2$ yields the formation of type 6 complexes (Scheme 4).

An example of an obtained type 6 complex (C17.2Et$_3$N) is depicted in Scheme 6.

Scheme 6

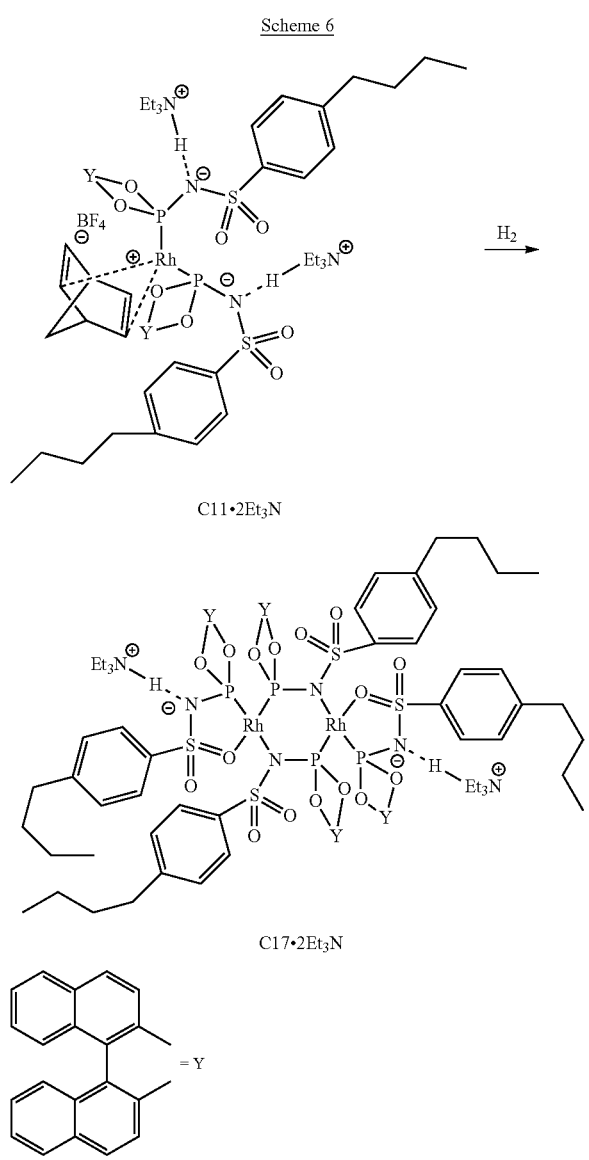

C11·2Et$_3$N

C17·2Et$_3$N

Still further, in defined cases, cationic complexes can be obtained of the type 7 by complexing one equivalent of ligand to one equivalent of a cationic metal precursor (Scheme 4). An example of a complex of this type is complex C14 that is depicted in Scheme 7. In this example one equivalent of L16 was added to [Rh(COD)$_2$](BF$_4$) to yield C14. Further examples of this type obtained include (FIG. 2) complexes C15 and C16.

Scheme 7

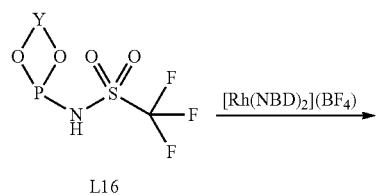

L16

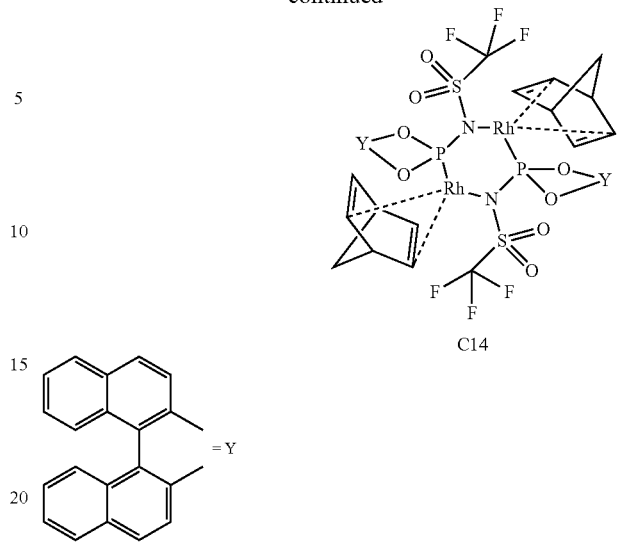

C14

Still further, coordination complexes containing a ligand to palladium are also feasible. For example, the complexation of two equivalents of L1 to PdCl$_2$(CH$_3$CN)$_2$ led to the formation of PdCl$_2$(L1)$_2$. Upon addition of 8 equivalents of Et$_3$N, the $^{31}$P signal showed the expected AB system attributed to PdCl(L1a,L1c) with the ligands coordinated in a cis-fashion. Complexation behavior of L1 to platinum is similar (FIG. 2, C18). This shows that the complexes of the invention can be prepared with different metals, such as rhodium, iridium, platinum, ruthenium and palladium.

The various rhodium complexes based on homo- and hetero-ligands can be applied in a range of asymmetric hydrogenation reactions; Table 1 through Table 6). In the asymmetric hydrogenation of acetamido acrylate, complexes based on ligand L8 provided the product in the highest ee (enantiomeric excess 99%, Table 1, entry 10). The hetero-ligand complex of Rh (L8.L1) was found to be the most active (TOF 1.2·10$^3$ mole/mole/h) and also selective (92% ee). All other mixed ligand systems using PPh$_3$ or aniline-S-(−)-1,1'-bis-2-naphthol-phosphoramidite (L18), provided the product with much lower enantio-selectivity. Kinetic experiments using Rh(L8.L1) complexes as the catalyst indicate that the reaction is zero order in molecular hydrogen (between 4-16 bar) and zero order in substrate (between 0.040 and 0.20 M) and is first order in rhodium (between 0.025 and 0.10 mM).

Further examples of coordination complexes containing a ligand used in rhodium or iridium catalyzed asymmetric hydrogenation of alkenes are listed in Table 2 through Table 6.

Further, coordination complexes containing a ligand can be used in the Rh catalyzed hydroformylation of alkenes (Table 7).

Still further, coordination complexes containing a ligand can be used in polymerization reactions, such as the Rh catalyzed polymerization of carbenes (for an example of this reaction using other catalysts see: Hettersheid, D. G. H.; et al.; *J. Am. Chem. Soc.*, (128), No. 30, 2006, 9746-9752. The Rh-catalyzed polymerization of EDA (ethyl diazoacetate) yielded the corresponding polymer with high molecular weight (Mw up to 475 kDa).

The coordination complex system of this invention can be immobilized onto an inorganic support, a polymeric organic support, or a hybrid support, wherein per equivalent metal at least one equivalent of ligand, more preferably at least two equivalent of ligands, are immobilized.

The coordination complex system can be used as a catalyst, for example for hydroformylation, hydrogenation, transfer hydrogenation, hydrocyanation, polymerization, isomerization, carbonylation, cross-coupling, metathesis, CH activation, allylic substitution, aldol condensation, or Michael addition.

The invention is further illustrated by the following non-limitative examples.

General

Methyl-2-acetamidoacrylate, R-(+)-1,1'-bis-2-naphthol, chlorobisphenylphosphine, phosphorus trichloride, 4-butyl-benzene-1-sulfonamide, were purchased from Aldrich, Reuter Chemische Apparatbau, Aldrich, Aldrich, and Maybridge respectively. Rh(acac)(CO)$_2$ and Rh(nbd)$_2$BF$_4$ were purchased from Merck and Alfa, respectively. Styrene, 1-octene, decane, and EDA (ethyl-diazoacetate) were all purchased from Aldrich. Synthesis of N-(1-phenyl-vinyl)-acetamide and related substrates are according: van den Berg, M. et al; *Adv. Synth. Catal.*, 2002, 344, 1003-1007.

All reactions were carried out in dry glassware under argon or nitrogen atmosphere. Every solution addition or transfer was performed via syringes. All solvents were dried and distilled with standard procedures.

Chromatographic purifications were performed by flash chromatography on silica gel 60-200 µm, 60 Å, purchased from Screening Devices. Chemical structures were confirmed by Nuclear Magnetic Resonance experiments which were performed on a Varian Inova spectrometer ($^1$H: 500 MHz, $^{31}$P: 202.3 MHz, $^{31}$C: 125.7 MHz). Chemical shifts were referenced to the solvent signal (7.27 ppm in $^1$H and 77.0 ppm in $^{13}$C NMR for CDCl$_3$). Conversions and enantiomeric excess for the asymmetric hydrogenation of methyl-2-acetamidoacrylate were determined by Gas Chromatography on a Phase PH MDEX-FT: 0.1 µm, length 5 m, inner diameter 0.1 mm. Conversions and enantiomeric excess for the asymmetric hydrogenation of dimethyl itaconate were determined by G.C. on a Supelco BETA DEX column (0.25 mm×30 m). Conversion and yields of the hydroformyation products were determined on a Shimadzu GC-17A apparatus (split/splitless, equipped with F.I.D. detector and a BPX35 column (internal diameter of 0.22 mm, film thickness 0.25 µm, carrier gas 70 kPa He)). Molecular distributions were measured using size exclusion chromatography (SEC) on a Shimadzu LC-20AD system with Waters Styragel HR1, HR2 and HR4 columns in series and a Shimadzu RID-10A refractive index detector using CH$_2$Cl$_2$ as mobile phase at 1 mL/min and T=313 K. Calibration was done using polystyrene standards in the range of 760 to 1,880,000 g/mole purchased from Aldrich.

Aniline-S-(−)-1,1'-bis-2-naphthhol-phosphoramidite: Ligand (L18) was prepared according to literature procedure (Lefort, L.; et al., *Org. Lett.*, 2004, 6, 1733-1735).

EXAMPLE 1

Synthesis of L1,
4-butylbenzene-1-sulfonamide-bisphenyl-phosphine

Commercially available 4-butylbenzene-1-sulfonamide (9.376 mole, 1 eq) was dissolved in tetrahydrofuran (20 mL) and triethylamine (25 mmole), leading to a clear colorless solution. Distilled chlorobisphenylphosphine (9.376 mmole, 1.0 eq) was added dropwise under strong magnetic stirring at room temperature. The suspension was left to stir overnight at room temperature. The suspension was then filtered under argon atmosphere and the resulting clear solution was evaporated to a white solid. The product was redissolved in 10 mL of diethylether leading to a clear solution. 10 mL of pentane were added dropwise to the solution causing a white solid to crash out. The organic layer was syringed out, and the white solid obtained was washed twice with 10 mL of pentane. The product was filtered over a short silica gel column with dichloromethane as eluent. The product was obtained as white solid. The product was characterized by $^1$H, $^{31}$P, $^{13}$C NMR.

EXAMPLE 2

Synthesis of L2:
benzenesulfonamide-bisphenylphosphine

Commercially available benzenesulfonamide (21.630 mmole, 1 eq) was dissolved in tetrahydrofuran (75 mL). The resulting solution was cooled at 0° C. nBuLi (1.02 eq, commercial solution 2.5 M in hexanes) was added dropwise leading to a white suspension. The suspension was stirred at room temperature for 30 min. The suspension was cooled at 0° C. and commercial Ph$_2$PCl (1.01 eq) was added dropwise. The clear solution obtained was stirred overnight at room temperature. The solvent was then evaporated. The crude product was dissolved in 40 mL of dichloromethane (DCM), and filtered over a plug of SiO$_2$ under argon. The plug was washed 5 times with 20 mL of DCM, and once with 20 mL of ethyl acetate (EA). All organic layers were united and evaporated to a sticky oil. Co-evaporation in Et$_2$O (twice 40 mL) lead to a white powder.

The product was characterized by $^1$H, $^{31}$P, $^{13}$C NMR.

EXAMPLE 3

Synthesis of L3:
4-butylbenzene-1-sulfonamide-disopropyl-phosphine

Commercially available 4-butylbenzene-1-sulfonamide (9.376 mole, 1 eq) was dissolved in tetrahydrofuran (40 mL), and cooled down at 0° C. nBuLi (1.1 eq, commercial solution 2.5 M in hexanes) was added dropwise. The white suspension obtained was stirred at room temperature for 10 min. The suspension was cooled at 0° C. and commercial iPr$_2$PCl was added dropwise. The clear solution obtained was stirred overnight at room temperature. The solvent was then evaporated yielding a white foam. The crude product was submitted to diethyl ether (Et$_2$O, 40 mL), yielding a white suspension. The suspension was filtered under argon over celite. The organic fractions were united and evaporated to a light yellow oil. The crude product was dissolved in toluene (10 mL) and evaporated. The crude product was then dissolved in Et$_2$O (5 mL). Hexanes (5 mL) were then added causing a precipitate to form. The solvents were evaporated, and the slightly yellow solid was washed thrice in hexanes (40 mL each time). The slightly yellow product was then dissolved in Et$_2$O (40 mL), and evaporated without heating means. The combined increase in concentration and loss in temperature caused the product to precipitate. The evaporation process was stopped at half volume, and the cold and slightly yellow Et$_2$O layer was syringed out. The process was repeated twice with 15 mL of Et$_2$O each time. The white powder obtained was characterized by $^1$H and $^{31}$P NMR.

EXAMPLE 4

Synthesis of L4:
4-methoxybenzene-1-sulfonamide-bisphenyl-phosphine

4-Methoxybenzene-1-sulfonamide (10.683 mmole, 1 eq) was dissolved in tetrahydrofuran (40 mL), and cooled down at 0° C. nBuLi (1.02 eq, 2.5 M in hexanes) was added dropwise. The white suspension obtained was stirred at room temperature for 30 min, cooled to 0° C. and $Ph_2PCl$ was added dropwise. The clear solution obtained was stirred overnight at room temperature. After removal of the solvents, the product was obtained as a white powder by $SiO_2$ gel chromatography (hexanes/ethyl acetate (7:3)). Isolated yield: 9.3%. The product was characterized by $^1H$, $^{31}P$, and $^{13}C$ NMR.

EXAMPLE 5

Synthesis of L5: rac-4-butylbenzene-1-sulfonamide-P-phenyl-P-anisyl-phosphine $hPCl_2$ (44.2 mmole, 1 eq) was diluted in diethyl ether ($Et_2O$, 400 mL) and cooled at 0° C. Diethylamine ($Et_2NH$, 88.8 mmole, 2 eq) was added dropwise. The resulting suspension was stirred overnight at room temperature, filtered and rac-Ph-$Et_2N$—PCl was obtained in quantitative yield (determined by $^{31}P$ NMR). (44 mmole, 1 eq) of nBuLi (2.5 M in hexanes) was added dropwise to a solution of ortho-bromoanisyl (44 mmole, 1 eq) in 15 mL of tetrahydrofuran (THF) at −78° C. The solution was then stirred at room temperature for 1 hour. The $Et_2O$ solution of rac-Ph-$Et_2N$—PCl previously prepared was cooled down at −78° C. and the anisyl-lithium salt was added dropwise and stirred overnight at room temperature. The resulting solution was then evaporated, and the product was extracted from $H_2O$ in dichloromethane (DCM). The product: rac-Ph-Anisyl-P($NEt_2$) was obtained as a slightly yellow and thick oil. The product was characterized with $^{31}P$ NMR. Isolated yield: 93%. rac-Ph-Anisyl-P($NEt_2$) (8.283 mmole, 1 eq) was dissolved in 80 mL of toluene/HCl solution (0.2 M of HCl, previously prepared by bubbling HCl gas in toluene). The resulting blur solution was stirred 1 hour at room temperature. The product: rac-Ph-anisyl-PCl was obtained quantitatively and characterized by $^{31}P$ NMR. The solution was reduced by evaporation of the toluene to ⅔ of the original volume, and 40 mL of hexanes were added leading to a suspension. The solution was filtered.

Commercially available 4-butylbenzene-1-sulfonamide (8.283 mmole, 1 eq) was dissolved in tetrahydrofuran (15 mL), and $Et_3N$ (32.525 mmole, 3.9 eq) was added. The previously prepared solution of rac-Ph-Anisyl-PCl was added to it dropwise and left to stir overnight. The solvents were then evaporated. The product was purified by $SiO_2$ gel chromatography in (toluene/ethyl acetate (9:1)). The white powder obtained was characterized by $^1H$, $^{31}P$, and $^{13}C$ NMR. (isolated yield (with respect to the commercial sulfonamide): 34%.)

EXAMPLE 6

Synthesis of L6: 4-butylbenzene-1-sulfonamide-P-phenyl-P-3-(R-2,2'-bimethoxynaphthyl)phosphine (diastereomeric mixture)

R-(+)-1,1'-bis-2-methoxynaphthyl, prepared from commercial R-(+)-1,1'-bis-2-naphthol and methyl iodine according to literature (*Journal of Molecular Catalysis, A: chemical*, 2005, p. 59-67) (15.905 mmole, 1 eq) was dissolved in 315 mL of tetrahydrofuran (THF) leading to a clear colorless solution. The solution was cooled at 0° C. and nBuLi (1.05 eq, commercial solution 2.5 M in hexanes) was added dropwise under strong magnetic stirring, yielding a clear dark yellow solution. After 1 hour stirring at 0° C., A solution of rac-Ph-$Et_2N$-PCl (15.9 mmole, 1 eq solution in $Et_2O$ (see Example 5) was added dropwise leading to a light colored clear solution. After 1 hour stirring at room temperature, the solvents were evaporated. The product was extracted from $H_2O$/dichloromethane, dried and isolated under reduced pressure. The product was purified over a $SiO_2$ plug upon subsequent washing with dichloromethane and ethyl acetate. The product was obtained as a white foam, identified in the $^{31}P$ and $^1H$ NMR as a mixture of RR— and RS—P-phenyl-P-3-(R-2,2'-bimethoxynaphthyl)POH. Isolated yield: 25%. The previous secondary phosphine oxide was then dissolved in 15 mL of $PCl_3$ and refluxed at 100° C. for 2 hours. After cooling back at room temperature, the $PCl_3$ was evaporated to obtain the product as a white foam. The product was dissolved in 25 mL of THF. The product was characterized with $^{31}P$ NMR, and identified as a 1 to 1 mixture of the RR— and RS—P-phenyl-P-3-(R-2,2'-bimethoxynaphthyl)PCl, obtained in a quantitative yield. 4-butyl-benzene-1-sulfonamide (4.190 mmole, 1.1 eq) was dissolved in tetrahydrofuran (40 mL), and cooled down at 0° C. nBuLi (1.1 eq, 2.5 M in hexanes) was added dropwise. The white suspension obtained was stirred at room temperature for 10 min, cooled to 0° C. and the solution of RR— and RS—P-phenyl-P-3-(R-2,2'-bimethoxynaphthyl)PCl was added dropwise. After overnight stirring at room temperature, the solvent was evaporated, and the crude product was purified with $SiO_2$ gel chromatography (toluene/ethyl acetate (9:1)). A white powder was obtained and characterized with $^1H$, $^{31}P$, $^{13}C$ NMR, mass spectrometry, and X-ray diffraction. Isolated yield: 48%, mixture of the RR and RS diastereoisomers.

EXAMPLE 7

Synthesis of L7: 4-butylbenzene-1-sulfonamide-P,P'-bis-3,3'-(R-2,2'-bimethoxynaphthyl)phosphine $PCl_3$ (14.314 mmole, 1 eq) was diluted in 150 mL of diethyl ether. The solution was cooled down at 0° C. and $Et_2NH$ (28.629 mmole, 2.0 eq) was added dropwise. The suspension obtained was stirred overnight at room temperature and filtered (intermediate characterized in $^{31}P$ NMR, identified as ($Et_2N$)$PCl_2$ obtained in a quantitative yield). R-(+)-1,1'-bis-2-methoxynaphthyl (28.629 mmole, 2.0 eq) was dissolved in THF, cooled to 0° C. and nBuLi (1.02 eq, commercial solution 2.5 M in hexanes) was added dropwise, yielding a clear dark yellow solution. After 1 hour stirring at 0° C., the previously prepared solution ($Et_2N$)$PCl_2$ was added dropwise leading to a light colored clear solution. After 1 hour stirring at room temperature, the solvents were evaporated. The product was then purified over a $SiO_2$ plug (subsequent DCM/EtOAc).The product (white solid) was characterized by $^1H$ and $^{31}P$ NMR, and identified as P,P'-bis-3,3'-(R-2,2'-bimethoxynaphthyl)-POH. Isolated Yield ($PCl_3$): 25%.

The previously obtained secondary phosphine oxide (3.379 mmole, 1 eq) was dissolved in 40 mL of $PCl_3$ and refluxed at 100° C. for 3 hours. The $PCl_3$ was then evaporated leading to a yellow sticky foam. The product was finally dissolved in 25 mL of tetrahydrofuran. The product was characterized in $^{31}P$ NMR and identified as P,P'-bis-3,3'-(R-2,2'-bimethoxynaphthyl)-PCl, obtained in a quantitative yield.

Commercially available 4-butylbenzene-1-sulfonamide (7.434 mmole, 2.2 eq) was dissolved in tetrahydrofuran (60 mL), and cooled down at 0° C. nBuLi (2.2 eq, commercial solution 2.5 M in hexanes) was added dropwise. The white suspension obtained was stirred at room temperature for 10 min. The suspension was cooled at 0° C. and the previously prepared solution of P,P'-bis-3,3'-(R-2,2'-bimethoxynaphthyl)-PCl was added dropwise. After overnight stirring at room temperature, the solvent was evaporated, and the crude product was purified with SiO$_2$ gel chromatography in dichloromethane. The product was obtained as a white powder, characterized by $^1$H, $^{31}$P and $^{13}$C NMR, as well as by mass spectrometry. Isolated yield: 53%.

EXAMPLE 8

Synthesis of L8(R), 4-butylbenzene-1-sulfonamide-R-(+)-1,1'-bis-2-naphthol-phosphoramidite Trichlorophosphine (12 mL, distilled) was added to a suspension of R-(+)-1,1'-bis-2-naphthol (9.647 mmole, 1.03 eq) in toluene. The mixture was heated up to 80° C. yielding a clear colorless solution which was left to stir overnight. The solution was then cooled down to room temperature and evaporated leading to white sticky foam. The sticky foam obtained was then dissolved in 10 mL of tetrahydrofuran leading to a clear colorless solution.

Procedure A: In a second Schlenk flask was placed 4-butylbenzene-1-sulfonamide (9.376 mmole, 1 eq) under argon atmosphere, dissolved in tetrahydrofuran (25 mL) and triethylamine (57 mmole) leading to a clear colorless solution. The solution of R-(+)-1,1'-bis-2-naphthol-PCl previously prepared was added drop wise to the amide solution at room temperature. The suspension obtained was left to stir overnight at room temperature and subsequently to obtain a white foam under educed pressure. The product was triturated in toluene. The product was obtained with a quantitative yield as a thin white powder.

Procedure B: In a second Schlenk flask was placed 4-butylbenzene-1-sulfonamide (9.376 mmole, 1 eq) was dissolved in tetrahydrofuran (90 mL) and nBuLi (1.01 eq, 2.5 M in hexanes) was added dropwise at 0° C. The white suspension obtained was stirred vigorously at room temperature for 30 min. The suspension was cooled at 0° C. and the R-(+)-1,1'-bis-2-naphthol-PCl solution was added dropwise. The clear solution obtained was stirred overnight at room temperature. The solvent was then evaporated to yield a white foam. The crude product was dissolved in diethyl ether (Et$_2$O, 45 mL), leading to a white suspension. The suspension was filtered under argon atmosphere over a dry layer of celite. The clear solution collected was evaporated to a white solid. The crude product was then dissolved in 5 mL of Et$_2$O, and evaporated again. The process was repeated 7 times, until the formation of a white powder that no longer dissolves. The ether layer was removed, and the resulting white powder was washed thrice with 10 mL of ether. Isolated yield: 20%, product characterized by $^1$H and $^{31}$P NMR.

Synthesis of L9-L16 were analogous to that of L8.

EXAMPLE 9

Synthesis of L17:
P-(4-butylbenzene-1-sulfonamide)-P-phenyl-XANTPhos

Xanthene (19.023 mmole, 0.49 eq) was dissolved in diethyl ether (Et$_2$O, 115 mL) and cooled down at 0° C. N,N', N'',N'''-tetramethylethyldiamine (TMEDA, 38.997 mmole, 1.00 eq) was added, and then nBuLi (38.997 mmole, 1.00 eq, 2.5 M in hexanes) was added dropwise. The resulting dark brown solution was stirred at room temperature for 18 hours. A solution of rac-Ph-Et$_2$N—PCl (39 mmole in Et$_2$O (see Example 5) was then added dropwise to afford a bright orange solution. The product was characterized in $^{31}$P NMR as a mixture of meso- and rac-P-Et$_2$N—P-phenyl-XANTPhos in a close to quantitative yield. The solution was then quenched with 300 mL of HCl solution (2M) and the Et$_2$O layer was separated. The aqueous phase was further extracted with ethyl acetate, yielding a light yellow oily product. The product was then dissolved in a toluene/hexanes 1 to 1 mixture (500 mL), and evaporated. The product was washed with Et$_2$O and the resulting foamy product obtained under educed pressure. The white powder obtained was characterized with $^{31}$P and $^1$H NMR and identified as a 1 to 1 mixture of meso- and rac-P-hydroxy-P-phenyl-XANTPhos. Isolated yield: 59%. The P-hydroxy-P-phenyl-XANTPhos previously prepared (9.969 mmole, 1 eq), was dissolved in commercial PCl$_3$ (30 mL) and refluxed overnight at 90° C. The PCl$_3$ was then evaporated to a light orange foam. The product was then dissolved in 10 mL of toluene and evaporated. The orange foam obtained was finally dissolved in 25 mL of tetrahydrofuran. The product was characterized in $^{31}$P NMR and identified as a 1 to 1 mixture of mesa- and rac-P—Cl—P-phenyl-XANTPhos in a close to quantitative yield. Commercially available 4-butylbenzene-1-sulfonamide (20.037 mmole, 2.01 eq) was dissolved in tetrahydrofuran (70 mL), and cooled down at 0° C. nBuLi (21.039 mmole, 2.11 eq, commercial solution 2.5 M in hexanes) was added dropwise. The white suspension obtained was stirred at room temperature for 1 hour. The previously prepared solution of meso- and rac-P—Cl—P-phenyl-XANTPhos was added dropwise under strong magnetic stirring. The clear orange solution obtained was stirred overnight at room temperature. The solvent was then evaporated leading to an orange foam. The product was purified over SiO$_2$ gel chromatography (toluene/ethyl acetate (9:1)). The white powder obtained was characterized by $^1$H, and $^{31}$P NMR.

EXAMPLE 10

Synthesis of Cl, Rh(L1a.L1c)(CO)

Typically: Ligand (L1) (0.03501 mmole, 2.00 eq) and commercially available Rh(acac)(CO)$_2$ (0.01745 mmole, 1.00 eq) were placed in a small Schlenk tube under argon atmosphere. CDCl$_3$ (4.1404 g, 2.7603 mL) was dropped on them leading to a clear yellow solution (6.325 mM of [Rh]). 600 µL of this solution were transferred to the NMR tube under argon conditions. In a similar fashion, complex Rh(L1)$_2$(CO) (complex 3) was studied in toluene-D8. All the characteristic couplings were found identical, showing that the solvent has little influence on the conformation and angles of the H-bonded supramolecular multidentate structure. The identification of the NH signal of the Rh(L1)$_2$(CO) structure was proven with a H—P 2D correlation spectra set at $J_{H-P}$=16 Hz. A solution of Rh(1)$_2$(CO) solution (9.959 mM in CDCl$_3$) was prepared as previously described and the H—P correlation was measured ($^1$H NMR 500 MHz, 223K).

Complexes C2-C6 were prepared analogous to C1.

EXAMPLE 11

Synthesis of C7; Rh(L8.L1c)(CO)

Ligand (11) (0.01957 mmole, 0.99 eq), ligand (L8) (0.02036 mmole, 1.03 eq), and Rh(acac)(CO)$_2$ (0.01970 mmole, 1.00 eq) were placed in a small Schlenk tube under argon atmosphere. CDCl$_3$ (540 µL) was added leading to a clear bright yellow solution, which was transferred in an NMR tube under argon atmosphere. A typical AB system was obtained in $^{31}$P NMR: complex (4), with 95% purity.

Complexes C8 and C9 were prepared analogous to C7.

EXAMPLE 12

Synthesis of C10; [Rh (L2)(Ph₂POH)(CO)]₂

Ligand (L2) (0.01957 mmole, 0.99 eq), commercial Ph₂POH (0.02036 mmole, 1.03 eq), and Rh(acac)(CO)₂ (0.01970 mmole, 1.00 eq) were placed in a small Schlenk tube under argon atmosphere. CD₂Cl₂ (500 µL) was added leading to a clear yellow solution, which was transferred in an NMR tube under argon atmosphere. The complex was characterized by ³¹P, ¹H NMR and X-ray diffraction. (Removal of the released AcacH was achieved by co-evaporation in toluene).

EXAMPLE 13

Synthesis of C11.2Et₃N; [Rh(L8.Et₃N)₂](BF₄)

Ligand L8.Et₃N (0.32103 mmole, 2.00 eq), and Rh(nbd)₂BF₄ (0.16051 mmole, 1.00 eq) were placed in a small Schlenk tube under argon atmosphere. CD₂Cl₂ (500 µL) was added leading to a dark brown solution, which was transferred to an NMR tube under argon atmosphere. The structure of C11.2Et₃N was identified by means of ¹H and ³¹P NMR and mass analysis.

Complex C12 was prepared analogous to C11.2Et₃N.

EXAMPLE 14

Synthesis of C13; Rh(L1)₂BF₄

An orange solution of 0.05350 mmole of C12 in CD₂Cl₂ (500 -µL) was transferred to a high pressure NMR tube under argon atmosphere. The resulting mixture was submitted to 6 bar of H₂, to afford C13 by hydrogenation of the alkene. The complex was characterized by ¹H, ³¹P NMR and mass spectrometry.

EXAMPLE 15

Synthesis of C15; [Rh(L8)(NBD)]₂

Ligand L8-Et₃N (0.01963 mmole, 1.05 eq), and Rh(nbd)₂BF₄ (0.01871 mmole, 1.00 eq) were placed in a small Schlenk tube under argon atmosphere. CD₂Cl₂ (500 µL) was added leading to a dark purple solution, which was transferred in an NMR tube under argon atmosphere. A typical AA'XX' 4 spin system was obtained in ³¹P NMR: complex C15, in a quantitative yield.

Complexes C14 and C16 were obtained in an analogous fashion

EXAMPLE 16

Synthesis of C17.2Et₃N; [Rh(L8.Et₃N)₂]₂

Ligand L8.Et₃N (0.32103 mmole, 2.00 eq), and Rh(nbd)₂BF₄ (0.16051 mmole, 1.00 eq) were placed in a small Schlenk tube under argon atmosphere. CD₂Cl₂ (500 µL) was added leading to a dark brown solution, which was transferred to a high pressure NMR tube under argon atmosphere. The resulting complex (C11.2Et₃N) was submitted to 6 bar of H₂, to afford C17.2Et₃N by hydrogenation of the alkene and subsequent ion exchange. The complex was characterized by ¹H, ³¹P NMR and mass spectrometry.

EXAMPLE 17

Synthesis of C18; Pt(L1)₂Cl₂

Ligand L1 (0.05047 mmole, 1.99 eq), and Pt(cod)Cl₂ (0.02538 mmole, 1.00 eq) were placed in a small Schlenk tube under argon atmosphere. CDCl₃ (500 µL) was added leading to a orange solution, which was transferred to a high pressure NMR tube under argon atmosphere. The complex, identified in ³¹P NMR as Pt(L1)₂Cl₂ was characterized with ³¹P, ¹H NMR and X-ray diffraction.

EXAMPLE 18

Comparative experiment with aniline-S-(−)-1,1'-bis-2-naphthol-phosphoramidite: as the H-bond donor ligand L18:

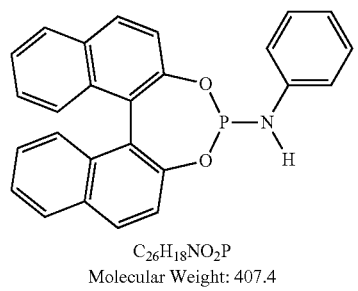

C₂₆H₁₈NO₂P
Molecular Weight: 407.4

Ligand (L1) (0.00704 mmole, 1.00 eq), ligand (L18) (0.00703 mmole, 1.00 eq), and Rh(acac)(CO)₂ (0.00704 mmole, 1.00 eq) were placed in a small Schlenk tube under argon atmosphere. CDCl₃ (1.1097 g, 740 µL) was dropped on it leading to a clear orange solution. The solution was transferred to the NMR tube under argon atmosphere. The ³¹P NMR profile afforded only homo-combined coordinated species.

General procedure for the asymmetric hydrogenation of methyl-2-acetoamidoacrylate, dimethyl itaconate and N-(1-phenyl-vinyl)-acetamide:

Typically: a 15 mL pressure reactor containing a glass insert was subsequently charged, under inert conditions, with 0.50 mL of a solution of ligand, 0.50 mL of a solution of ligand (2), 0.50 mL of solution of Rh(nbd)₂BF₄, and 1.0 mL of solution of substrate, all of dichloromethane at the required concentrations. The 2.5 mL of resulting solution was then stirred at room temperature for 5 minutes. The solution was then exposed to 10 bar of H₂ atmosphere, and left to stir at room temperature (298 K) for 8 hours (vortex-type stirring: 400 rpm). Conversions and enantio-selectivities were determined by chiral GC.

General procedure for the rhodium catalyzed asymmetric hydrogenation with monitoring gas uptakes:

The experiments were carried out in the AMTEC SPR16 (www.amtec-chemnitz.de) consisting of 16 parallel reactors equipped with temperature and pressure sensors, and a mass flow controller. The apparatus is suited for monitoring gas uptake profiles during the catalytic reactions.

Three autoclaves were heated to 90° C. and flushed with argon (22 bar) five times. Next the reactors were cooled to 25° C. and flushed again with argon (22 bar) five times. The autoclaves were charged with 0.80 µmole of [Rh(nbd)$_2$(BF$_4$)] and 1.92 µmole of phosphorus ligand(s) in 3.00 mL of dichloromethane under argon. The reaction mixtures were mixed for 30 minutes at 25° C., before 800 µmole of the substrate in 5.0 mL of dichloromethane were added under argon. The reactors were pressurized with 10 bar H$_2$ and the pressure was kept constant during the whole reaction. The reaction mixtures were stirred at 25° C. for 13 h and the hydrogen uptake was monitored and recorded for every reactor. After catalysis the pressure was reduced to 2.0 bar and samples (0.3 mL) were taken.

In Table 1 an overview is given for some Rh-catalyzed asymmetric hydrogenation of methyl-2-acetamido acrylate.

TABLE 1

Rhodium catalyzed hydrogenation of methyl-2-acetoamido acrylate, entry 4 and 11 have been added as control experiments.

| Entry | Ligand combination | [Rh] (mM) | Substrate/Rh | ee (%) | R/S | TOF |
|---|---|---|---|---|---|---|
| 1 | L1 | 1 | 100 | 0 | — | — |
| 2 | L1/L8 | 1 | 100 | 90.6 | S | — |
| 3 | L8 | 1 | 100 | 95.8 | S | — |
| 4 | PPh$_3$ | 1 | 100 | 0 | — | — |
| 5 | PPh$_3$/L18 | 1 | 100 | 13.3 | S | — |
| 6 | L18 | 1 | 100 | 62.1 | R | — |
| 7 | L1/L18 | 1 | 100 | 41.7 | R | — |
| 8 | L1 | 0.1 | 1000 | 0 | — | 6.5*10$^2$ |
| 9 | L1/L8 | 0.1 | 1000 | 91.7 | S | 1.2*10$^3$ |
| 10 | L8 | 0.1 | 1000 | 99.0 | S | 5.7*10$^2$ |
| 11 | PPh$_3$ | 0.1 | 1000 | 0 | — | — |
| 12 | PPh$_3$/L18 | 0.1 | 1000 | 3.6 | S | — |
| 13 | L18 | 0.1 | 1000 | 65.0 | R | — |
| 14 | L1/L18 | 0.1 | 1000 | 46.0 | R | — |

Rh/(L8)/(L1) = 1/1.2/1.2 in CH$_2$Cl$_2$, 10 bar H$_2$, 8 h at 298 K, full conversion for all entries, ee (enantiomeric excess) determined by chiral GC, TOF(turnover frequency: mole/mole)/h) determined from gas uptake profiles at 20% conversion.

Further examples include the rhodium catalyzed hydrogenation of dimethyl itaconate (Table 2) and of N-(1-phenyl-vinyl)-acetamide (Table 3)

TABLE 2

Rhodium catalyzed hydrogenation of dimethyl itaconate.

| Entry | Ligand combination | [Rh] (mM) | Conversion (%) | ee (%) | R/S |
|---|---|---|---|---|---|
| 1 | L1 | 1 | 100 | 0 | — |
| 2 | L1/L8 | 1 | 96.5 | 51.6 | R |
| 3 | L8 | 1 | 15.2 | 48.3 | R |

Rh/(L) = 1/2.6 in CH$_2$Cl$_2$, 10 bar H$_2$, 8 h at 298 K, Substrate/Rh = 100, ee determined by chiral GC.

TABLE 3

Rhodium catalyzed hydrogenation of N-(1-phenyl-vinyl) acetamide.

| Entry | Ligand combination | [Rh] (mM) | Conversion (%) | ee (%) | R/S |
|---|---|---|---|---|---|
| 1 | L1/L8 | 1 | 100.0 | 56.0 | R |
| 2 | L8 | 1 | 77.0 | 48.7 | R |

Rh/(L) = 1/2.4 in CH$_2$Cl$_2$, 10 bar H$_2$, 16 h at 298 K, Substrate/Rh = 100, ee determined by chiral GC.

Still further are included examples of asymmetric hydrogenations using a different rhodium precursor (table 4)

TABLE 4

Rhodium catalyzed hydrogenation of a range of substrate using Rh (acac) (ethylene)$_2$ as the precursor unless else stated*

| Entry | Ligand | Substrate | Time (hour) | Pressure H$_2$ (bar) | Conversion (%) | ee (%) |
|---|---|---|---|---|---|---|
| 1 | L8.Et$_2$O | I | 20 | 30 | 17 | 79 |
| 2 | L8.Et$_2$O | II | 20 | 10 | 0 | — |
| 3 | L8.Et$_2$O | III | 15 | 20 | 100 | 45 |
| 4 | L8.Et$_2$O | IV | 18 | 30 | 32 | 5 |
| 5 | L8.Et$_3$N$^a$ | I | 15 | 30 | 27 | 13 (R) |
| 6 | L8.Et$_2$O$^a$ | I | 15 | 30 | 21 | 57 |
| 7 | L8.Et$_2$N$^b$ | I | 15 | 30 | 57 | 6 (R) |
| 8 | L8.Et$_2$O$^b$ | I | 15 | 30 | 60 | 23 |
| 9 | L16.thf | I | 16 | 30 | 92 | 0 |

*[Rh]: 5 mM, [L]: 11 mM, [Substrate]: 100 mM, solvent is CH$_2$Cl$_2$, temp.: 298 K. ee deteremined by chiral GC or chiral HPLC,
$^a$Rhodium precursor was [Rh (acac) (COE)$_2$],
$^b$Rhodium precursor was [Rh (acac) (COD)$_2$]

The procedure for the iridium catalyzed asymmetric hydrogenation of trimethyl indolinene is analogous to that of the rhodium catalyzed processes.

TABLE 5

Iridium catalyzed hydrogenation of trimethyl indolinene*

| Entry | Combined ligands | [Ir] (mM) | Conversion (%) | ee (%) | R/S |
|---|---|---|---|---|---|
| 1 | L1/L8 | 1 | 73.5 | 71.7 | R |
| 2 | L8 | 1 | 4.6 | 64.1 | R |

*Ir/L ratio: 1/2.4, iridium precursor: [Ir(COD)Cl]$_2$, 10 bar H$_2$, 12 h at 298 K, substrate/Rh = 100, ee determined by chiral HPLC.

TABLE 6

Iridium catalyzed hydrogenation of ethyl styrene*

| Entry | ligand | [Ir] (mM) | Conversion (%) | ee (%) |
|---|---|---|---|---|
| 1 | L8•THF | 0.5 | 98 | 4 |
| 2 | L7 | 0.5 | 2 | 5 |
| 3 | L16•Et$_3$N | 0.5 | 12 | 4 |

*Ir/L ratio: 1/1.1, iridium precursor: [Ir(COD)$_2$](BArF), 40 bar H$_2$, 12 h at 298 K, substrate/Rh = 100, ee determined by chiral HPLC.

General procedure for the Rh-catalyzed hydroformylation of styrene:

Rh(acac)(CO)$_2$ (0.0031 mmole, 1 eq), Ligand (0.0239 mmole, 7.7 eq), toluene (2.5 mL), Styrene (previously filtered over basic alumina, 3.002 mmole, 968 eq) and decane (internal standard, 0.990 mmole) were placed in a small Schlenk tube under argon, leading to a clear yellow solution. The resulting solution was placed in a suited 5 mL glass reactor equipped with a matching stirring bean, which was placed inside the autoclave. The autoclave was purged thrice with 15 bar of H$_2$/CO (1:1), then submitted to 15 bar of H$_2$/CO for 20.5 h at 333 K. The autoclave was then cooled down in an ice-bath, depressurized and a sample was prepared for the GC.

TABLE 7

Rhodium catalyzed hydroformylation of styrene*

| Entry | Ligand | Conversion (%) | B:L |
|---|---|---|---|
| 1 | L2 | 100 | 21.5 |
| 2 | L3 | 100 | 18.3 |
| 3 | L10 | 100 | 21.1 |

*Rh/L/styrene: 10/22/1000 mM, solvent DCM, reaction time 15 h, Rh: [Rh(acac)(CO)$_2$], temp. 40° C. pressure: 20 bar CO/H$_2$ ; B:L = branched:linear General Procedure for the Rh-Catalyzed Hydroformylation of 1-octene:

Rh(acac)(CO)$_2$ (0.0013 mmole, 1 eq), Ligand (0.0123 mmole, 9.5 eq), toluene (1.95 mL) and decane (internal standard, 4.2019 mmole) were place inside a 15 mL reactor autoclave with a suited magnetic bean under argon atmosphere. The resulting solution was incubated for 56 min at 343K and 10 bar of H$_2$/CO (1:1). The 1-octene (previously filtered over basic alumina, 8.3577 mmole, 6429 eq) was added in a toluene solution (2.14 mL) via syringe. The resulting solution was submitted to 10 bar of H$_2$/CO at 343 K for 4 hours under strong magnetic stirring. The autoclave was then cooled with an ice bath, depressurized and a sample was injected on GC. The conversion was found at 10.74% (isomers: 28.23%, linear aldehyde: 49.62%) and 2.24 as linear/branched aldehyde ratio.

General Procedure for the Rh-Catalyzed Polymerization of EDA (Ethyl-Diazoacetate):

Rh(acac)(CO)$_2$ (0.0774 mmole, 1 eq) and ligand (0.1628 mmole, 2.1 eq) were placed under argon in a small Schlenk tube. CH$_2$Cl$_2$ (10 mL) were added leading to a clear yellow solution. EDA (4.34 mmole, 56 eq) was then added under strong magnetic stirring at room temperature. Immediately a strong degassing was observed, and the resulting orange solution was left to stir overnight at room temperature. The solvent was then evaporated to a sticky product. Cold MeOH (10 mL) was then added leading to a white suspension into an orange solution. The product was centrifuged, and the MeOH removed. The polymer was washed twice more with cold MeOH, and then submitted to vacuum. The white solid obtained (isolated yield: 3.5%) was analyzed on GPC and yielded a Mw/Mn of 18.5 for a Mw of 475 kDa.

The invention claimed is:

1. A coordination complex system comprising a ligand having the formula:
   R$_1$—SO$_2$—NH—P(XR$_2$)$_2$; or
   R$_1$—SO$_2$—N═PH(XR$_2$)$_2$; or
   R$_1$—SO(OH)═N—P(XR$_2$)$_2$,
   wherein X is independently O, S, NH, or a bond; R$_1$ and R$_2$ are independently selected from hydrogen and substituted or unsubstituted alkyl or aryl; and
   wherein at least one equivalent of the ligand is complexed to an equivalent of a metal selected from a transition metal and lanthanide.

2. The coordination complex system of claim 1, wherein R$_1$ is selected from C$_{1-6}$ alkyl and aryl, which aryl is unsubstituted or substituted by at least one of alkyl, alkoxy, nitro, tri-C$_{1-4}$ alkylsilyl, CF$_3$, and halogen, and which C$_{1-6}$ alkyl is optionally substituted by halogen; and
   R$_2$ is selected from C$_{1-6}$ alkyl and aryl, which aryl is unsubstituted or substituted by at least one of alkyl, alkoxy, nitro, tri-C$_{1-4}$ alkylsilyl, CF$_3$, and halogen, and which C$_{1-6}$ alkyl is optionally substituted by halogen; or
   wherein two moieties R$_2$ together form a divalent aryl, optionally substituted with at least one of alkyl, alkoxy, nitro, tri-C$_{1-4}$ alkylsilyl, CF$_3$, and halogen; or
   wherein two ligands, if each of the ligands have at least one R$_2$ is aryl, are connected to each other through said two aryl groups by one or two linking moieties, selected from N, O, S, and one or two carbon atoms, wherein the N is bonded to H or C$_{1-6}$ alkyl, and the carbon atom or atoms are bonded to H and/or C$_{1-6}$ alkyl.

3. The coordination complex system of claim 2, wherein R$_1$ is CF$_3$ or phenyl, which phenyl is unsubstituted or substituted with at least one of alkyl, alkoxy, nitro, tri-C$_{1-4}$ alkylsilyl, CF$_3$, and halogen, and R$_2$ is phenyl, bisphenyl, naphthyl, or bisnaphthyl, which phenyl, bisphenyl, naphthyl, and bisnaphthyl groups are unsubstituted or substituted with at least one of alkyl, alkoxy, nitro, tri-C$_{1-4}$ alkylsilyl, CF$_3$, and halogen; or
   wherein X═O and two moieties R$_2$ together form a divalent phenyl, divalent bisphenyl, divalent naphthyl, or divalent bisnaphthyl group optionally substituted with at least one of alkyl, alkoxy, nitro, tri-C$_{1-4}$ alkylsilyl, CF$_3$, and halogen; or
   wherein two ligands, if each of these ligands have at least one R$_2$ is phenyl, are connected to each other through said two phenyl groups by one or two linking moieties, selected from N, O, S, and one or two carbon atoms, wherein the N is bonded to H or C$_{1-6}$ alkyl, and the carbon atom or atoms are bonded to H and/or C$_{1-6}$ alkyl.

4. The coordination complex system of claim 3, wherein R$_1$ is CF$_3$ or phenyl which is optionally substituted by C$_{1-6}$ alkyl, CF$_3$, NO$_2$, C$_{1-6}$ alkoxy, or halogen, and R$_2$ is independently C$_{1-6}$ alkyl, phenyl, bisnaphthyl, wherein phenyl and bisnaphthyl is optionally substituted by C$_{1-6}$ alkoxy, CF$_3$, or halogen; or X═O and both R$_2$ moieties together form a bisnaphthyl group which is optionally substituted by C$_{1-6}$ alkoxy, CF$_3$, or halogen.

5. The coordination complex system of claim 4, wherein R$_1$ is CF$_3$, phenyl or 4-n-butyl substituted phenyl, 4-CF$_3$, 4-NO$_2$, 4-OCH$_3$, 4-Br, 2,3,4,5,6-pentafluoro, or 3,5-di-CF$_3$ substituted phenyl, and R$_2$ is independently isopropyl, phenyl, methoxy-substituted phenyl, bisnaphthyl, or methoxy-substituted bisnaphthyl, or X═O and both R$_2$ moieties together form a bisnaphthyl.

6. The coordination complex system of claim 1, wherein the transition metal is selected from rhodium, iridium, platinum, ruthenium and palladium.

7. The coordination complex system of claim 1, wherein at least one equivalent of ligand 1 is immobilized onto an inorganic support, a polymeric organic support, or a hybrid support.

8. A catalyst system comprising the coordination complex system of claim 1.

9. A method of catalyzing a reaction comprising adding to the reaction the coordination complex system of claim 1.

10. The method of claim 9, wherein the reaction is hydroformylation, hydrogenation, transfer hydrogenation, hydrocyanation, polymerization, isomerization, carbonylation, cross-coupling, metathesis, CH activation, allylic substitution, aldol condensation, or Michael addition.

* * * * *